United States Patent [19]

Dehnel

[11] 4,392,908
[45] Jul. 12, 1983

[54] PROCESS FOR MAKING ABSORBENT ARTICLES

[75] Inventor: Roger B. Dehnel, Sharnbrook, England

[73] Assignee: Lever Brothers Company, New York, N.Y.

[21] Appl. No.: 223,864

[22] Filed: Jan. 9, 1981

[30] Foreign Application Priority Data

Jan. 25, 1980 [GB] United Kingdom ............... 8002624

[51] Int. Cl.³ .................... B32B 31/00; C09J 5/00; B22F 3/00
[52] U.S. Cl. ............................ 427/194; 156/291; 156/309.3; 156/324.4; 156/283; 427/222; 427/208.2; 427/201; 427/180; 428/407; 428/311.1; 264/112; 604/378
[58] Field of Search ............... 156/284, 313, 279, 283, 156/290, 291, 309.6, 324.4, 182, 70, 179, 307.5, 309.3; 260/17.4 ST, 17.4 GC; 427/222, 208.2, 203, 206, 180, 189, 195, 200, 201; 428/403, 349, 283; 524/504; 527/312

[56] References Cited

U.S. PATENT DOCUMENTS

| | | | |
|---|---|---|---|
| 2,902,395 | 9/1959 | Hirschy et al. | 156/284 |
| 4,156,664 | 5/1979 | Skinner et al. | 524/504 |
| 4,243,696 | 1/1981 | Toth | 427/180 |
| 4,297,410 | 10/1981 | Tsuchiya | 156/283 |

FOREIGN PATENT DOCUMENTS

| | | |
|---|---|---|
| 2222780 | 7/1975 | Fed. Rep. of Germany . |
| 1376392 | 1/1972 | United Kingdom . |
| 2004201 | 3/1979 | United Kingdom . |

Primary Examiner—Edward C. Kimlin
Assistant Examiner—Louis Falasco
Attorney, Agent, or Firm—James J. Farrell

[57] ABSTRACT

The invention concerns a process for manufacturing a water-absorbent article in which particles of a water-swellable polymer are fixed to a water-absorbent substrate. The process includes the steps of forming on the surface of the water-swellable particles a coating of a thermoplastic adhesive resin; locating the coated particles in their unswollen and dry state on or within the water-absorbent substrate also in the dry state; and applying heat to soften the thermoplastic coating of the particles and pressing the particles and substrate to cause the particles to be bound to the substrate.

5 Claims, No Drawings

PROCESS FOR MAKING ABSORBENT ARTICLES

This invention relates to a process for making an absorbent article, e.g. for use in sanitary products, and is more particularly concerned with the fixing of particles of a water-swellable material to a substrate.

It is well known to enhance the capacity of various products, such as sanitary towels, tampons, babies' nappies and dressings, to absorb body fluids by incorporating therein particles of a highly water-swellable material.

There is, however, a problem in fixing the particles of the water-swellable material at the desired site. According to one known method, the substrate to which the swellable particles are applied, or the particles themselves, or both, are wetted or dampened with water or steam and thereafter the mixture is dried; such a procedure is described in British Specifications Nos. 1,345,561 (Dow Chemical Co.), 1,345,406 (Dow Chemical Co.) and 1,576,475 (Unilever), and U.S. Pat. Nos. 3,645,836 (Torr) and 4,096,312 (Hoechst AG). In the procedure according to British Specification No. 1,376,392 (Dow Chemical Co.) the water-swellable particles are first treated with a water-soluble cationic polymer to improve the adhesion of the particles to the substrate.

These processes have the disadvantage that they require the use of apparatus for the application of the water or steam and apparatus for drying the coated substrates, and are thereby relatively complex methods of effecting the fixing of the absorbent particles to the substrate.

In British Specification No. 2,004,201 (Beghin-Say) an aqueous solution of polyvinyl alcohol or acrylic latex is applied, e.g. by spraying, to a deposit of absorbent particles on a substrate. The use of an acrylic latex for securing a highly absorbent polymer to a substrate is also described in U.S. Pat. No. 4,156,664 (Henkel Corp.) according to which the absorbent is applied to the substrate dispersed in the acrylic latex.

In a method described in German Specification No. 22 22 780 (Schickedanz) the absorbent particles are first mixed with particles of a thermoplastic such as polyethylene, the mixture applied to the substrate and heat is applied to soften the thermoplastic. The softened thermoplastic has a soldering action and, on cooling, the thermoplastic acts to secure the particles to the substrate and to each other.

We have shown that the above processes relying upon the use of a plastic to bind the absorbent particles to the substrate have a substantial deleterious effect upon the wicking properties of the substrate/absorbent particle composite.

It is an object of the invention to provide an improved process for manufacturing a water-absorbent article in which particles of a water-swellable polymer are fixed to a substrate of a water-absorbent material.

According to the present invention there is provided a process for manufacturing a water-absorbent article in which particles of a water-swellable polymer are fixed to a water-absorbent substrate, which process comprises:

1. forming on the surface of the water-swellable particles a coating of a thermoplastic adhesive resin;
2. locating the coated particles in their unswollen and dry state on or within the water-absorbent substrate also in the dry state; and
3. applying heat to soften the thermoplastic coating of the particles and pressing the particles and substrate to cause the particles to be bound to the substrate.

Many synthetic substantially water-insoluble absorbent polymers having a high capacity for absorbing water and body fluids have been developed in recent years and these may be used in the process of the invention. Some of these polymer are partially synthetic and some wholly synthetic. Among the partially synthetic absorbent polymers are those based on starch. These include the starch-acrylo-nitrile graft copolymers described in U.S. Pat. Nos. 3,997,484 (the U.S.A. as represented by the Secretary of Agriculture) and 3,661,815 (Grain Processing Corporation) and the cross-linked gelatinised starch derivatives described in British Patent Specification No. 1,576,475 (Unilever) and U.S. Pat. No. 4,117,222 (Hoechst AG). Other examples of partially synthetic absorbent polymers are the cross-linked carboxymethylated cellulose ethers described in U.S. Pat. Nos. 3,589,364 (Buckeye Cellulose Corporation), 3,936,441 (Hoechst AG) and 3,965,091 (Hoechst AG). Other examples of partially synthetic absorbent polymers are the cross-linked carboxymethylated cellulose ethers described in U.S. Pat. Nos. 3,589,364 (Buckeye Cellulose Corporation), 3,936,441 (Hoechst AG) and 3,965,091 (Hoechst AG), as well as the carboxymethylcellulose cross-linked by acid interesterification as described by Podlas, T. J., in INDA Tech Symp. 1975, 2-3 Mar. pp 25-39.

Wholly synthetic absorbents include polyacrylates cross-linked with a polyamide/epichlorhydrin material as described in British patent specification No. 1,549,994 (Dow Chemical Co.) and the potassium salts of polyacrylic acid cross-linked by aluminium ions as described in U.S. Pat. No. 4,090,013 (National Starch & Chemical Corporation).

The thermoplastic used to form the coating on the particles of the absorbent material may, for example, be an acrylic acid or acrylate polymer, such as a copolymer of styrene and acrylic acid. Vinyl thermoplastic resins such as poly(vinyl acetate) or poly(vinyl alcohol) may also be used. Thermoplastics which are not cross-linked by heat are preferred. The thermoplastic used is desirably one whose surface becomes tacky and adhesive at temperatures above about 80° C. Thermoplastics which are sufficiently brittle to permit their being milled are also desirably used since in the production of the thermoplastic coated particles a milling stage will generally be necessary. It is, of course, required that the coating of the particles of the water-swellable polymer with the thermoplastic should be effected so that the coated particles retain a substantial capacity for absorbing fluids. Thermoplastics used should therefore be ones which form films which allow the passage of water or which form low wet strength bonds. Highly hydrophobic thermoplastics are unsuitable. Desirably, the coated particles of the absorbent polymers should have an absorbency efficiency of at least 75%. The absorbency efficiency of a coated absorbent is related to the extent to which the thermoplastic coating may modify the absorbency of the water-swellable polymer itself. It is calculated from the urine retention values for the coated and uncoated swellable polymer, respectively, and takes account of the proportion of the thermoplastic, based on the absorbent polymer, constituting the coating. The percentage absorbency efficiency of a thermoplastic-coated swellable polymer absorbent is given by the expression $URV_{A+P}(100+x)/URV_A$ where $URV_{A+P}$ is the urine retention value for the coated absorbent particles, $URV_A$ is the urine retention value of the absorbent polymer itself, and x is the percentage by weight of the thermoplastic based on the weight of the absorbent polymer. The coated particles preferably have an absorbency efficiency of at least 90%. The absorbency efficiency may exceed 100% in cases where the thermoplastic itself has absorptive properties. Urine retention values are determined by the method described in British Specification No. 1,576,475.

The particles of the absorbent material can be coated with the thermoplastic resin by any suitable technique. One method which is satisfactory is to thoroughly mix the absorbent particles with an aqueous latex of the resin and then dry the mixture. Other methods include spraying a resin solution or latex onto particles of absorbent material. Furthermore, the resin may be added to the particles when the particles are in a slurry, for example in an organic solvent, the resin being added either in water or an organic solvent such as methanol. It may also be possible to incorporate the thermoplastic as a solution or latex during the manufacture of the absorbent material so as to produce as the end product thermoplastic coated absorbent particles. It will usually be necessary to mill the particles after application of the thermoplastic so as to produce a free-flowing powder.

The amount of thermoplastic is desirably such that the weight ratio of thermoplastic to water-swellable polymer is 1:20 to 1:1.

The water-absorbent substrate to which the particles are to be bound may be composed of cellulose fluff, tissue paper, textile fibres or non-woven materials.

In the process of the invention the procedure for effecting the attachment of thermoplastic coated particles to the substrate involves a heating and pressing stage, the heating being required to soften the thermoplastic coating on the absorbent particles and application of pressure being required to effect the securing and bonding of the thermoplastic to the substrate. The passage of the coated substrate through the nip of a pair of rollers at least one of which is heated is a convenient method of carrying out the necessary heating and pressing operations.

The invention will now be illustrated by reference to Examples 1 to 4 according to the invention and Comparative Examples A to E. Further embodiments of the invention are illustrated in Examples 5 to 11. Percentages are by weight.

EXAMPLE 1

This example concerns the use, in the manufacture of an absorbent article, of particles of a water-absorbent cross-linked carboxymethylated starch absorbent coated with a poly(vinyl alcohol).

The water-absorbent starch derivative was made generally in accordance with the procedure described in Example 2 of British Specification No. 1,576,475 save that immediately prior to the final ammoniation stage, the acid-washed gel cake was mixed with a 15% solution of poly(vinyl alcohol) (average molecular weight 14,000). The proportions of acid gel cake and solution of poly(vinyl alcohol) were such that the poly(vinyl alcohol) amounted to 10% of the final starch derivative, calculated on a dry weight basis. The mixture was then dried using circulating air at 80° C. and the polymer-coated particles hammer-milled through a 2 mm screen. The product obtained had a urine retention value of 9.6 g/g. The uncoated absorbent starch derivative itself, obtained without the addition of the poly (vinyl alcohol) solution, had a urine retention value of 10.1 g/g. The absorbency efficiency (as defined herein) of the thermoplastic-coated absorbent was therefore 104%.

The dry coated particles were then used to produce a laminate as described with reference to FIG. 1 of the drawing of British Specification No. 1,576,475 except that no water spray device 10 or heating chamber 11 were employed. However, in this present case the roller 4 was of steel rather than rubber and rollers 3 and 4 were heated to about 160°–190° C. The heat from the rollers softened the thermoplastic coating on the starch particles and the pressure applied by the rollers caused the particles to be bound to the two layers of tissue material which were thereby secured to each other. The paper tissues each had a weight of 22 gm$^{-2}$. The laminate produced comprised 100 gm$^{-2}$ of actual starch-based absorbent material.

EXAMPLE 2

In this example the procedure described in Example 1 was followed except that an amount of poly(vinyl alcohol) solution was employed to give 24% of the plastic based on the starch derivative iself. The thermoplastic coated absorbent material obtained also had a urine retention value of 9.6 g/g corresponding to an absorbency efficiency of 118%.

EXAMPLE 3

In the procedure of this Example, the thermoplastic used to form the coating on the water-absorbent particles was a poly(vinyl acetate) available commercially in the form of an aqueous latex from Vinyl Products Limited under the trade name "Vinamul 9000". This was diluted to 15% solids before use. The thermoplastic coated absorbent starch derivative was made otherwise as described in Example 1, the amount of the thermoplastic being 18% based on the starch derivative. The coated particles had a urine retention value 8.1 g/g corresponding to an abosorbency efficiency of 95%.

The particles of the thermoplastic coated absorbent starch derivative were then employed in the formation of a laminate of tissues in the same manner as described in Example 1 above.

EXAMPLE 4

In the procedure of this example, the thermoplastic used to form the coating on the water-absorbent particles was a non-cross-linking styrene-acrylic copolymer available commercially in the form of an aqueous latex from Vinyl Products Limited under the trade name "Vinacryl 7170". The latex was diluted to 15% solids before use. The thermoplastic coated absorbent starch derivative was made following the procedure of Example 1, the latex replacing the poly(vinyl alcohol) solution. The amount of the latex used was such that the thermoplastic was 18% of the starch derivative itself, calculated on the dry basis. The coated particles had a urine retention value of 6.8 g/g corresponding to an absorbency efficiency of 79%.

Laminates were formed from these coated particles in the same way as in Example 1 above.

Comparative Examples A to C

A laminate was formed of two sheets of the tissue material referred to above with particles of the uncoated starch-based absorbent materials referred to in Example 1 between them, the absorbent amounting to 100 gm$^{-2}$ of the laminate. The laminate was sprayed with a resin solution or latex and then left to dry, giving an amount of applied thermoplastic of 18 gm$^{-2}$. The solution and latices employed are indicated in Table I.

TABLE I

| Comparative Example | Solution/Latex |
|---|---|
| A | Solution of Example 1 |
| B | Latex of Example 3 |
| C | Latex of Example 4 |

Comparative Examples D and E

Particles of the uncoated starch-based absorbent referred to in Example 1 were mixed with particles of a thermoplastic resin and the mixture formed as a layer between two layers of tissues as used in the above experiments. The laminate was then passed between the nip of a pair of hot rollers which so softened the plastic and compressed the laminate whereby the absorbent particles were bonded to the tissues. The absorbent resin mixture was such that the laminate contained 100 gm$^{-2}$ of the starch absorbent and 18 gm$^{-2}$ of thermoplastic. The thermoplastics employed are indicated in Table II.

TABLE II

| Comparative Example | Thermoplastic |
|---|---|
| D | Vinyl acetate/ethylene copolymer (18:82)[1] |
| E | Polyvinyl alcohol[2] |

[1] Available commercially from ICI Ltd under the trade name "Alkathene 18150.039".
[2] The same as used to form the solution in Example 1.

The urine retention values for the combinations of absorbent and resin particles employed in Comparative Examples D and E were 8.1 g/g and 8.8 g/g, respectively.

The laminates produced according to the procedures described in Examples 1 to 4 and Comparative Examples A to E were tested by the wicking test described below. Also tested was a laminate made by the wet route described with reference to FIG. 1 of British Specification No. 1,576,475 and employing the uncoated cross-linked starch derivative and tissues referred to in Example 1 above. This comparative wet route laminate and all the laminates of Examples 1 to 4 and Comparative Examples A to E contained the same weight (100 g) per square meter of the actual starch-based absorbent.

Wicking Test

In this test strips (width 25 mm) of a laminate were suspended from one end in a 1% solution of sodium chloride. The height reached by the liquid and the weight of the liquid taken up into the strip after 5 minutes of wicking were recorded. In each instance, five samples were used and the average value taken.

Wicking Test Results

Table III below gives the results of the wicking test on the laminates obtained according to Examples 1 to 4 and Comparative Examples A to E and includes the results for the wet-route laminate.

TABLE III

| Laminate | Wicking Height (mm) | Wicking Weight (g) |
|---|---|---|
| Example 1 | 75 | 2.89 |
| Example 2 | 83 | 3.13 |
| Example 3 | 76 | 2.71 |
| Example 4 | 55 | 2.45 |
| Comparative Example A | 21 | 0.80 |
| Comparative Example B | 33 | 1.27 |
| Comparative Example C | 42 | 1.74 |
| Comparative Example D | 22 | 0.40 |
| Comparative Example E | 46 | 1.23 |
| Wet-route laminate | 67 | 2.56 |

It can be seen that the use of a thermoplastic resin in accordance with the invention for securing an absorbent to a carrier results in a product having a greater facility to take up liquid than a product made by the known procedures of the comparative examples.

The laminates of the examples and the wet-route laminate were also tested by an absorbency test and a percentage retention efficiency value (as defined herein) determined.

Laminate Absorbency Test

In this test, samples of the laminates were tested for total absorbency by the urine retention test described in British Specification No. 1,576,475. Two samples were used in each case and the mean value taken.

From the urine retention value of the laminate, the retention efficiency of the combination of the absorbent material and thermoplastic within the laminate was calculated as a percentage of the urine retention value of the combination of absorbent material and thermoplastic prior to incorporation in the laminate. Thus the percentage retention efficiency (%RE) is given by the expression $$\% RE = \frac{URV_{A+P}'}{URV_{A+P}} \times 100$$

where $URV_{A+P}$ is the urine retention value of the combination of the absorbent and thermoplastic prior to incorporation in the laminate and $URV_{A+P}'$ is the effective retention value of the combination of the absorbent material and thermoplastic within the laminate, where $$URV_{A+P}' = \frac{W_L}{W_A + W_P}\left[URV_L - URV_T \cdot \frac{W_T}{W_L}\right]$$

where
$W_L$ = weight of the laminate per square meter and equals $W_A + W_P + W_T$
$W_A$ = weight of the absorbent per square meter of laminate
$W_P$ = weight of the thermoplastic per square meter of laminate
$W_T$ = weight of the tissue per square meter of laminate
$URV_L$ = urine retention value of the laminate
$URV_T$ = urine retention value of the tissue material In the experiments reported herein the values for $W_A$, $W_T$ and $URV_T$ were, respectively, 100 g, 44 g and 2 g/g.

Laminate Absorbency Test Results

Table IV below gives the results of the absorbency tests and includes the respective percentage retention efficiency values (%RE).

TABLE IV

| Laminate | URV$_L$ (g/g) | % RE |
|---|---|---|
| Example 1 | 7.3 | 91 |
| Example 2 | 7.0 | 98 |
| Example 3 | 6.3 | 100 |
| Example 4 | 5.3 | 100 |
| Comparative Example A | 5.4 | 78 |
| Comparative Example B | 4.8 | 68 |
| Comparative Example C | 5.0 | 71 |
| Comparative Example D | 4.8 | 72 |
| Comparative Example E | 5.6 | 86 |
| Wet-route laminate | 6.7 | 87 |

Concerning the above table, it is observed that in the case of Comparative Example A to C, where the powder incorporated in the laminate consisted entirely of the starch absorbent, in calculating the %RE value there was substituted for URV$_{A+P}$ in the expression for %RE, the value of URV$_A$, the urine retention value of the uncoated starch absorbent itself.

EXAMPLES 5 TO 8

These examples concern the modification of other absorbent materials by a thermoplastic. In each case the absorbent was slurried in methanol and a solution of Vinamul 9000 in methanol was added in sufficient quantity to give a mixture with 20% by dry weight of thermoplastic. The material was dried at 50° C. using circulating air and milled. Laminates can be produced from the modified absorbent particles by the procedure described in Example 1. Table V indicates the absorbent materials used in these examples. This table also gives the percentage absorbency efficiency (%AE) of the thermoplastic coated absorbent materials.

TABLE V

| Example | Absorbent | % AE |
|---|---|---|
| 5 | P | 94 |
| 6 | Q | 95 |
| 7 | R | 99 |
| 8 | S | 97 |

Absorbent P was the potassium salt of polyacrylic acid cross-linked by aluminium ions and commercially available from National Starch Corporation under the trade name Permasorb 30 and generally described in U.S. Pat. No. 4090013.

Absorbent Q was a hydrolysed cross-linked polyacrylonitrile available from Toho Beslon Co. Limited and generally described in Japanese patent applications Nos. 49394/77 and 9095/77.

Absorbent R was a hydrolysed starch-polyacrylonitrile graft copolymer available from the Grain Processing Corporation under the trade name Polymer 35-A-100 and generally described in U.S. Pat. No. 3,661,815.

Absorbent S was a vinyl alcohol/sodium acrylate copolymer available commercially from the Sumitomo Chemical Company under the trade name Hydrogel-S-50 and generally described in U.S. Pat. Nos. 4,102,842 and 4,155,893.

EXAMPLE 9

Particles of the thermoplastic coated absorbent starch as described in Example 3 were employed in the formation of a laminate in a manner similar to that described in Example 1 except viscose-cotton fleece as commonly used in tampon manufacture was employed. The fleece was a 70/30 mixture of viscose/cotton with fibre length 51 mm and weight 60 gm$^{-2}$.

EXAMPLE 10

Particles of the thermoplastic coated absorbent starch as described in Example 3 were employed in the formation of a laminate in a manner similar to that described in Example 1 except that two "non-woven" webs were used. The non-woven was a 22 gm$^{-2}$ viscose web with a styrene-butadiene binder.

EXAMPLE 11

Particles of the thermoplastic coated absorbent starch as described in Example 3 were mixed with wood pulp fluff and laid by means of an air stream onto a moving belt. After heating and compression the absorbent particles were located into the web.

What I claim is:

1. A process for manufacturing a water-absorbent article in which particles of a water-swellable polymer are fixed to a water-absorbent substrate, which process comprises:
   1. forming on the surface of the water-swellable particles a coating of a thermoplastic adhesive resin to form coated particles;
   2. locating the coated particles in their unswollen and dry state on or within the water-absorbent substrate also in the dry state; and
   3. applying heat to soften the thermoplastic coating of the particles and pressing the particles and substrate to cause the particles to be bound to the substrate.

2. A process as claimed in claim 1, wherein the thermoplastic coated absorbent particles have an absorbency efficiency of at least 75%.

3. A process as claimed in claim 1, wherein the weight ratio of the thermoplastic resin to the water-swellable polymer is from 1:20 to 1:1.

4. A process as claimed in claim 2, wherein the weight ratio of the thermoplastic resin to the water-swellable polymer is from 1:20 to 1:1.

5. A process as claimed in claim 1, wherein the coated particles are bound to the substrate by passing the water-absorbent substrate on or within which the coated particles have been located through the nip of pair of rollers at least one of which is heated.

* * * * *